United States Patent
Tsukashima et al.

(10) Patent No.: US 11,980,444 B2
(45) Date of Patent: *May 14, 2024

(54) METHODS AND DEVICES FOR COLOR DETECTION TO LOCALIZE THE BLOOD MASS OF AN INTRACEREBRAL HEMATOMA

(71) Applicant: Rebound Therapeutics Corporation, Irvine, CA (US)

(72) Inventors: Ross Tsukashima, Irvine, CA (US); Peter G. Davis, Irvine, CA (US)

(73) Assignee: Rebound Therapeutics Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/138,398

(22) Filed: Apr. 24, 2023

(65) Prior Publication Data

US 2023/0255494 A1  Aug. 17, 2023

Related U.S. Application Data

(63) Continuation of application No. 17/135,066, filed on Dec. 28, 2020, now Pat. No. 11,633,107, which is a
(Continued)

(51) Int. Cl.
*A61B 5/00* (2006.01)
*A61B 1/00* (2006.01)
*A61B 5/02* (2006.01)

(52) U.S. Cl.
CPC ........ *A61B 5/0086* (2013.01); *A61B 1/00052* (2013.01); *A61B 5/02042* (2013.01);
(Continued)

(58) Field of Classification Search
CPC .............. A61B 5/0086; A61B 1/00052; A61B 5/02042; A61B 5/4064; A61B 5/6851;
(Continued)

(56) References Cited

U.S. PATENT DOCUMENTS

| 4,502,487 A | 3/1985 | DuBrucq et al. |
| 6,324,418 B1 | 11/2001 | Crowley et al. |

(Continued)

FOREIGN PATENT DOCUMENTS

| CN | 101677784 | 3/2010 |
| CN | 102149334 | 8/2011 |

(Continued)

OTHER PUBLICATIONS

International Search Report and Written Opinion from International Application No. PCT/US2017/033175 dated Jul. 19, 2017.
(Continued)

*Primary Examiner* — Ashley K Buran
*Assistant Examiner* — Aminah Asghar
(74) *Attorney, Agent, or Firm* — Crockett & Crockett, PC; K. David Crockett, Esq.

(57) ABSTRACT

Devices for localizing an intracerebral hematoma or blood mass in brain tissue. The devices include an elongate probe a color sensors and a light emitter on the distal end of the probe. The color sensors produce a signal corresponding to the color of light reflected into the color sensors. A display is provided to indicate the color detected.

18 Claims, 4 Drawing Sheets

Related U.S. Application Data continuation of application No. 15/598,135, filed on May 17, 2017, now Pat. No. 10,874,303.

(60) Provisional application No. 62/337,498, filed on May 17, 2016.

(52) U.S. Cl.
CPC .......... *A61B 5/4064* (2013.01); *A61B 5/6851* (2013.01); *A61B 5/6852* (2013.01); *A61B 2505/05* (2013.01)

(58) Field of Classification Search
CPC . A61B 5/6852; A61B 2505/05; A61B 5/0084; A61B 5/742
See application file for complete search history.

(56) References Cited

U.S. PATENT DOCUMENTS

| | | | |
|---|---|---|---|
| 9,848,821 | B2 | 12/2017 | Rule et al. |
| 2004/0262507 | A1 | 12/2004 | Kikuchi et al. |
| 2005/0124918 | A1 | 6/2005 | Griffin et al. |
| 2008/0058591 | A1 | 3/2008 | Saadat et al. |
| 2008/0104855 | A1 | 5/2008 | Kim et al. |
| 2009/0149776 | A1 | 6/2009 | Adams |
| 2010/0081964 | A1 | 4/2010 | Mark et al. |
| 2012/0302875 | A1 | 11/2012 | Kohring |
| 2014/0135609 | A1 | 5/2014 | Kostenich et al. |
| 2014/0339987 | A1 | 11/2014 | Burrows et al. |
| 2015/0105769 | A1 | 4/2015 | Igarashi et al. |
| 2015/0164390 | A1 | 6/2015 | Larvenz et al. |
| 2015/0258296 | A1 | 9/2015 | Pecherer |
| 2015/0297073 | A1 | 10/2015 | Nguyen et al. |
| 2016/0174848 | A1 | 6/2016 | Ammar |
| 2016/0239965 | A1 | 8/2016 | Kuramoto |
| 2016/0328848 | A1 | 11/2016 | Andre et al. |

FOREIGN PATENT DOCUMENTS

| | | |
|---|---|---|
| CN | 203436309 | 2/2014 |
| CN | 104114104 | 10/2014 |
| CN | 104434034 | 3/2015 |
| EP | 2057934 | 5/2009 |
| GB | 2345606 | 7/2000 |
| JP | 2004202252 | 7/2004 |
| JP | 20096118 | 1/2009 |
| JP | 201224595 | 2/2012 |
| JP | 2015231467 | 12/2015 |
| WO | WO2006050047 | 5/2006 |
| WO | WO2008057494 | 5/2008 |
| WO | WO2008146203 | 12/2008 |

OTHER PUBLICATIONS

Examination Report No. 1 from Australian Patent Application No. 2017268341 dated Feb. 1, 2019.
Partial European Search Report from European Patent Application No. 17800119.4 dated Dec. 19, 2019.
Examination Report No. 2 from Australian Patent Application No. 2017268341 dated Jan. 24, 2020.
Examination Report No. 3 from Australian Patent Application No. 2017268341 dated Jan. 29, 2020.
Extended European Search Report dated Mar. 30, 2020 from European patent application 17800119.4.
Australian Examination Report dated May 26, 2020 from Australian Patent Application No. 2020200655.
Notification of Reasons for Refusal dated Jul. 21, 2020 from Japanese Patent Application 2019-512945.
Office Action from Japanese Patent Application No. 2019512945 dated Nov. 9, 2020.
Korean Office Action from Korean Patent Application No. 1020187035751 dated Nov. 11, 2020.
First Office Action from Chinese Patent Application No. 201780042011.8 dated Nov. 25, 2020.
Office Action from European Patent Application No. 17800119.4 dated Jan. 20, 2021.
Summons to Attend Oral Proceedings dated Aug. 23, 2021 from European Patent Application 17800119.4.

METHODS AND DEVICES FOR COLOR DETECTION TO LOCALIZE THE BLOOD MASS OF AN INTRACEREBRAL HEMATOMA

This application is a continuation of U.S. application Ser. No. 17/135,066, filed Dec. 28, 2020, now U.S. Pat. No. 11,633,107, which is a continuation of U.S. application Ser. No. 15/598,135 filed May 17, 2017, now U.S. Pat. No. 10,874,303, which in turn claims priority to U.S. Provisional Application 62/337,498 filed May 17, 2016.

FIELD OF THE INVENTIONS

The inventions described below relate to the field of minimally invasive brain surgery.

BACKGROUND OF THE INVENTIONS

Stroke is a common cause of death and disabling neurologic disorder. Approximately 700,000 patients suffer from stroke in the United States every year. Hemorrhagic stroke accounts for 20% of the annual stroke population. Hemorrhagic stroke is due to a rupture of a blood vessel in the brain, causing bleeding into the brain tissue and resulting in a hematoma (a blood mass) in the brain. Prompt removal of the blood mass is necessary to limit or prevent long-term brain injury. Clear visualization and imaging of the blood mass and any surrounding surgical field facilitates removal of the blood mass. Removal and visualization can often be accomplished through a cannula and obturator assembly, placed through a hole drilled in the skull near the site of the hematoma. The site of the hematoma can be accurately identified using a CT scan. To aid in placement of the cannula and obturator assembly precisely at the hematoma, and also to aid in inserting the cannula through a route least likely to damage healthy brain tissue, neurosurgeons use sophisticated and costly stereotactic surgery systems or neuro-navigation systems. These systems depend on previously obtained MRI or CT scans, which may be several hours old, and thus not perfectly reflective of the shape and location of the blood mass at the time of surgery. In these systems, visual confirmation that the cannula distal end is properly positioned can be accomplished only after the obturator has been removed from the cannula. If the distal end has not been accurately placed, the obturator must be re-inserted, and the cannula and obturator assembly must be manipulated, perhaps repeatedly, until, after removal of the obturator, the blood mass is visible. A less sophisticated method, used before these expensive neuro-navigation systems and stereotactic systems became standard and still used where these systems are not available, involves large craniotomies, exploration and direct visual search for a blood mass, extensive tissue dissection, and invasive instrumentation, all associated with high mortality and morbidity.

SUMMARY

The devices and methods described below provide for a probe for localizing a blood mass in a patient's brain. The probe has one or more color sensors and a light emitter on the distal end and a display on the proximal end. The color sensors produce a signal corresponding to the characteristics of light reflected into the color sensors. A controller is operatively connected to the color sensors to convert the signal to data suitable for display to a user through the display, and the display is operatively connected to the controller for visualizing a color, data, one or more graphs and/or an audible signal corresponding to the tissue reflecting light to the color sensors. The display may be a simple light, operable to display color corresponding to the color sensed by the color sensors. This visual feedback is provided to the user of the probe during use, while the user is pushing the probe through the brain to reach and find a blood mass. The probe may be used alone, to locate a blood mass, or in combination with an aspirator to locate and then aspirate the blood mass, or in combination with a cannula or sheath (with the probe serving as an obturator), or as a guide wire or stylet for an aspiration catheter to be navigated into the brain, over the stylet, or in combination with a neuro-navigation system to confirm proper location after insertion of a probe or sheath under stereotactic or neuro-navigation guidance.

DETAILED DESCRIPTION OF THE INVENTIONS

Figure 1:
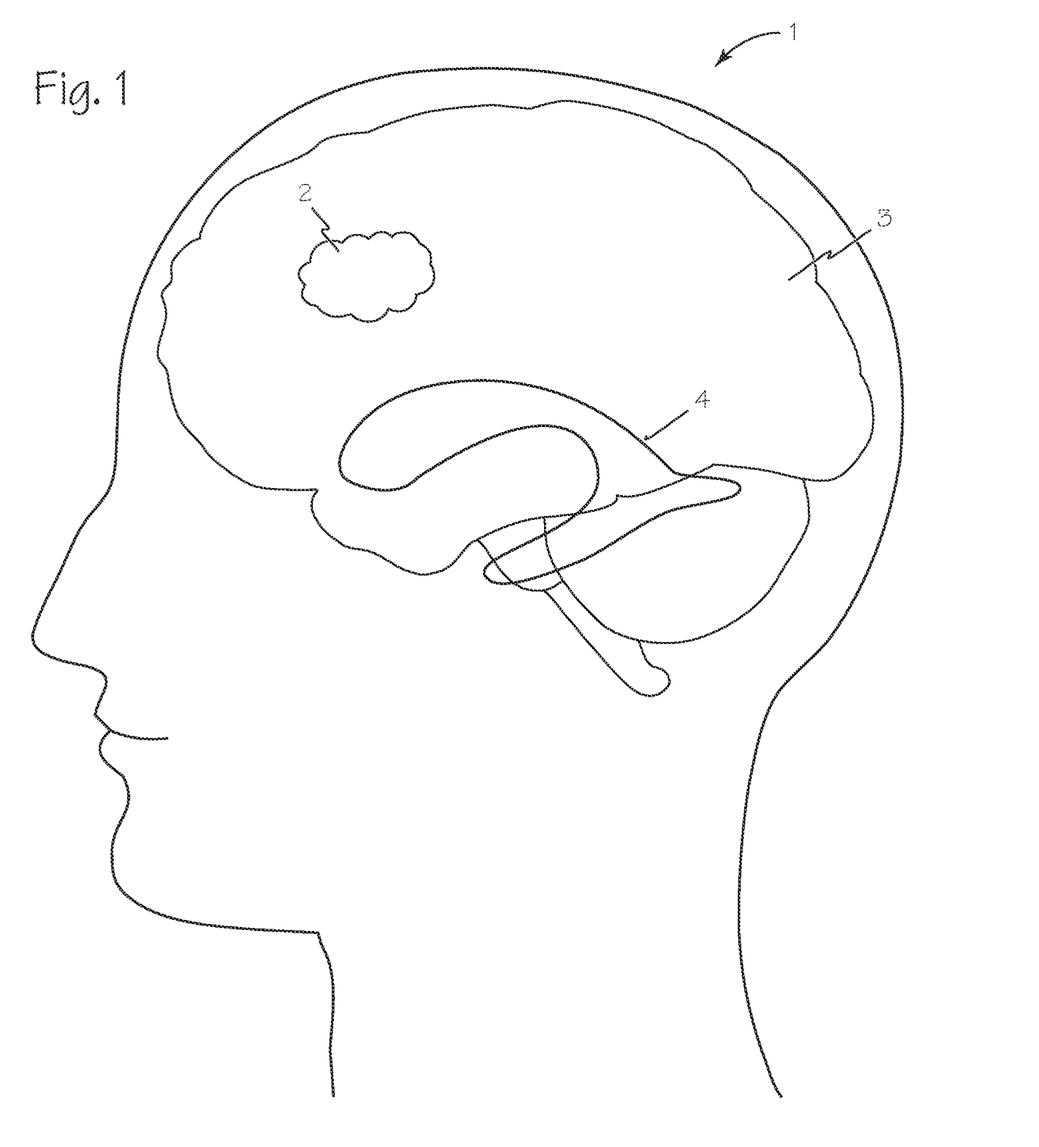
FIG. 1 illustrates a patient with an intracerebral hematoma.

FIG. 1 illustrates a patient 1 with an intracerebral hematoma or blood mass 2 in brain tissue 3. Blood and blood clots such as blood mass 2 are red to red/black, and the surrounding brain tissue 3 is white or off-white. The ventricles 4 contain cerebrospinal fluid, which is colorless. As described below, a probe fitted with a color sensor assembly can be used to navigate through the brain and detect when the probe tip enters the blood mass or the ventricles.

Figures 2, 3:
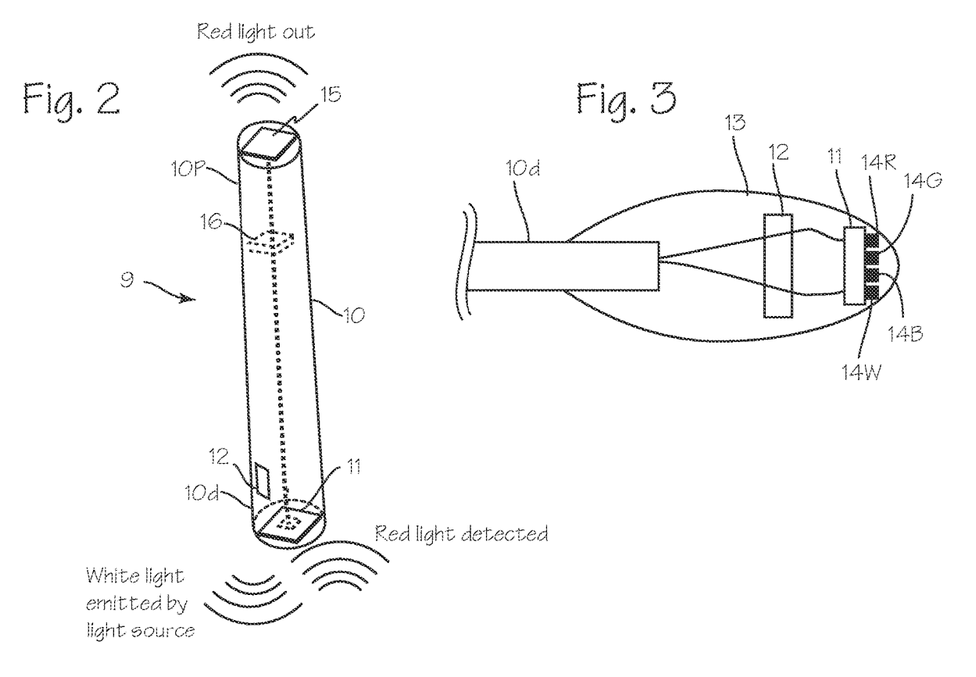
FIGS. 2 and 3 illustrate a blood mass localizer which includes a color sensor assembly.

FIG. 2 illustrates a blood mass localizer 9 which includes a probe comprising a slender rod 10 which has a proximal end 10p and a distal end 10d. The distal end is adapted for transcranial insertion into the brain of a patient. The proximal end resides outside the skull during use. The probe can comprise a cannula or trocar, an obturator or a sheath, a guide catheter, a stiff wire or probe, a needle, or an aspiration tube. The device illustrated in FIG. 2 is a simple probe, with a small diameter for the entire length of the device. The distal end 10d of the probe includes color sensor assembly 11 and one or more light sources such as light source 12 which produces white light and/or infrared light, or, at least, light of several wavelengths, or, in single color embodiments, a single-color light such as red. As shown in the detail view of FIG. 3, the color sensor assembly and the light source may be embedded in a clear lens or boss 13 of clear epoxy or plastic. Preferably, the light source is disposed proximal to the color sensor, as shown in FIG. 3. The color sensor assembly 11 includes one or more light sensors such as sensor 14R, 14G, 14B and 14W (shown in FIGS. 3 and 4), which sense light of different colors, which preferably include one or more of red, green, blue, and white (an infrared light sensor can also be included, for use as described below). Thus, the color sensor may be multi-color sensor or a single-color sensor. The proximal end 10p of the localizer includes a display 15, such as a multi-color LED, OLED or PLED array, which is operably connected to the sensor assembly 11 through a suitable controller 16. The controller is operable to receive signals from the color sensor assembly 11 (corresponding to intensity of light detected by each color sensor) and produce an output signal (or signals) corresponding to the color(s) detected by the color sensor assembly. The controller operates the display 15, such that the display displays a color that mimics the color of any light detected by the color sensor assembly 11. A battery or power source and circuitry needed to operate and power the color sensor, controller and display may be disposed anywhere in the device. The lens can be configured with additional optical elements, or augmented with prisms to direct light reflected from tissue off-axis from the longitudinal axis of probe and rod.

For "over-the-wire" use, the probe may consist of the rod, the color sensor assembly, the light source, which may be encapsulated in the lens, and the display and the controller, all disposed on or within a probe of small diameter suitable for insertion through brain tissue and subsequent insertion of a sheath, cannula or shunt over the probe (while the probe remains in the brain).

The color sensor assembly 11 is preferably an RGBW color sensor assembly with light sensor(s) 14R, 14G, 14B and 14W to detect light of various colors and produce signals corresponding to the detected colors (one or more frequencies or wavelengths and the intensity or power of light at the one or more frequencies or wavelengths incident on the sensors such as red, green, blue or white light, in the case of an RGBW sensor assembly). The color sensor assembly is preferably an RGBW (red-green-blue-white) color sensor assembly, but the system can be implemented with alternate color sensors such as RGB color sensors, cyan-magenta-yellow (CMY); cyan-magenta-yellow-black (CMYK); hue-saturation-value (HSV) or hue-saturation-lightness (HSL). The color sensor assembly produces signals corresponding to the frequency and intensity of the light incident on the sensors. For example, an RGBW color sensor provides signals corresponding to the intensity of red, green, blue and white light incidents upon the sensors. More sophisticated imaging devices, distinct from color sensors, such as CCD's, CIS or CMOS image sensors may be used, though full image data is not necessary. The controller 16 is operably connected to color sensor assembly 14 and optionally to light source 12, to operate the light source to emit light into surrounding body tissue (to illuminate the body tissue and cause reflected light to reach the sensors) and receive sensor data from each sensor (corresponding to the reflected light detected by each sensor) and convert it to a useful format (signal useful to operate the display) and forwards output signals to the display to cause the display to present information to a user corresponding to the color of tissue proximate the color sensor.

Figure 4:
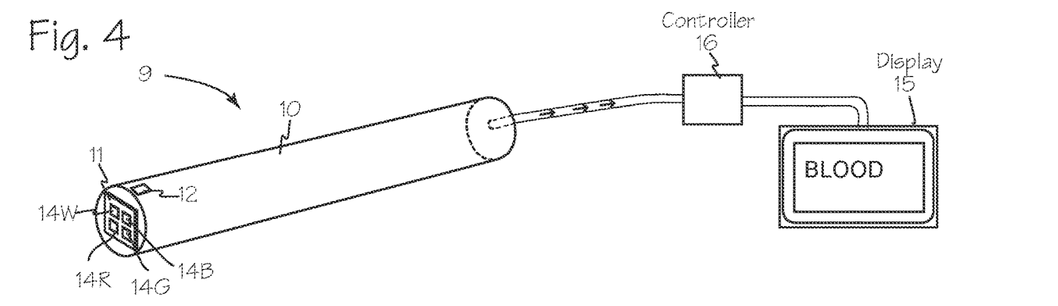
FIGS. 4 and 5 illustrate a blood mass localizer with a discrete display.
Figure 5:
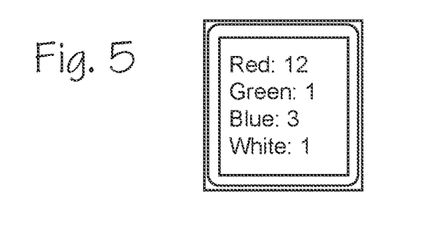

FIG. 4 illustrates a blood mass localizer 9 configured as an elongate probe which includes the color sensor assembly 11 and light source 12 and a textual display. As with the device of FIG. 2, the sensor assembly produces signals that the controller uses to produces output signals to the display to cause the display to present information to a user. In this system, the display 15 may be remote from the localizer, and may take the form of a computer display (such as a CRT, LED display, or the like) or a small LCD display. The controller may be located anywhere in the system. The color data provided to a user may be displayed as text describing body tissue matching the color detected by the color sensors, such as "BLOOD" or "BRAIN", or, as shown in FIG. 5, as one or more numbers corresponding to intensity of light received by each sensor, or as a color patch on the display, a series of color patches (one for each sensor) a bar graph, or any other useful indicia or image useful to communicate to a use the color of tissue proximate the color sensing assembly. The system may also include a speaker, operable by the controller, to provide audible prompts to the user corresponding to the color detected by the color sensing assembly. Additional color sensors may be positioned along the length of the probe, and around the circumference of the probe, to provide color feedback for tissue about the probe proximal to the distal tip of the probe.

FIGS. 6 through 10 illustrate the use of the blood mass localizer 9 to locate and map an intracerebral blood mass such as blood mass 2. This is illustrated with the localizer 6 in the configuration shown in FIG. 2.

Figure 6:
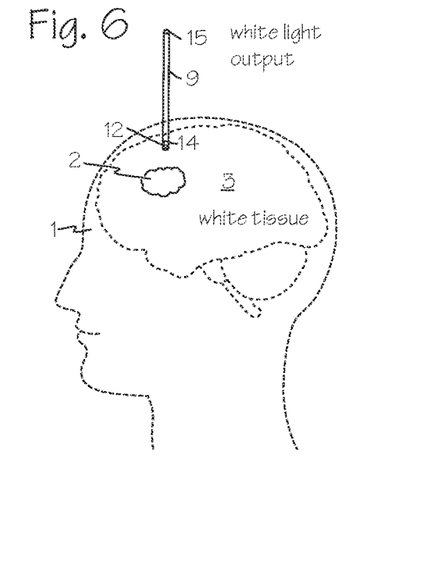
FIGS. 6 through 10 illustrate steps for localizing and removing the intracerebral blood mass from the patient of FIG. 6.
Figure 7:
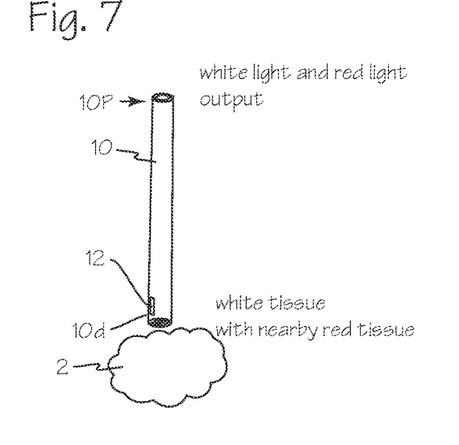
Figure 8:
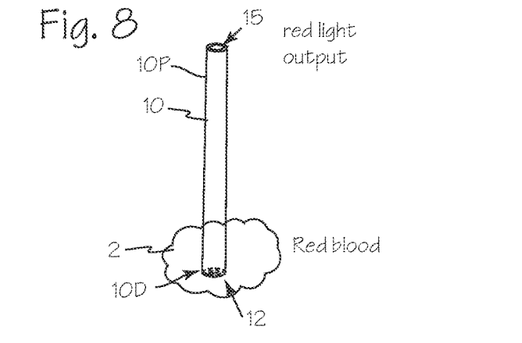
Figure 9:
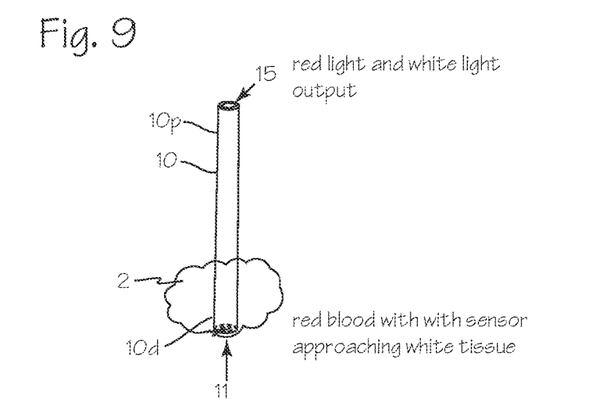

As shown in FIG. 6, a surgeon inserts distal end 10D of probe 10 with sensor assembly 11 on the distal end of the probe, to find and localize blood mass 2. The surgeon advances the probe through brain tissue 3 until reaching the blood mass 2, while operating the localizer, including operating the LED light source 12 to emit light into surrounding tissue and operating the color sensor assembly to detect any light reflected, and operating the display 15 to indicate the predominant color of reflected light incident on sensor assembly 11. When the color sensor assembly is disposed within brain tissue, which is white or off-white, the color sensor assembly detects this color, and the controller causes the display to illuminate the display, to emit corresponding white or off-white color. As the color sensor approaches the blood mass, as shown in FIG. 7, the color sensor will, detect increasing intensity of red light reflected from the blood mass transmitted back to the color sensor through the surrounding brain tissue. In this instance, the controller causes the display to illuminate the display, to emit corresponding pale red. Upon further advancement of the color sensor assembly, such that the color sensor assembly enters the blood mass as shown in FIG. 8, and the color sensor assembly detects the red color corresponding to blood mass, the controller causes the display to illuminate the display, to emit corresponding red. This indicates that color sensor assembly 11 is in the blood mass 2 as illustrated in FIG. 8. As illustrated in FIG. 8, the display 15 indicates a predominantly red color as long as sensor assembly 11 is within the blood mass 2. As the probe 10 is advanced through the brain and blood mass, the color sensor assembly 11 will eventually approach the distal margin of the blood mass and exit the blood mass as illustrated in FIG. 9. As the color sensor assembly 11 nears the margins of the blood mass, light reflected to color sensor assembly 11 begins losing the predominant red color, and the color emitted by display 15 (as controlled by the controller) changes to a pink color to suggest the nearing brain tissue 3. If advanced past the blood mass, such that the color sensor assembly re-enters brain tissue, the controller will cause the display to emit, again, a white or off-white color corresponding to the color of the brain tissue.

The controller may be configured or programmed to provide a display corresponding to detected color that, rather than closely mimic the detected color, indicates the detected color in a step-wise fashion. For example, the controller may be configured or programmed to emit red light indicative of a blood clot when the detected color is predominantly red (a combination of relative intensities and ratios of detected color, such as a ration of red to green greater than 1.5 and relative output count for red greater than 5000 (on a scale of 0 to 65000 as provided by a Vishay VEML6040 sensor).

With the controller configured or programmed and operated in this fashion, the display will not transition gradually from white to red when approaching the blood mass, but will shift to red quickly when the probe tip encounters blood (as indicated by reaching the threshold intensity of the detected red light).

Figure 10:
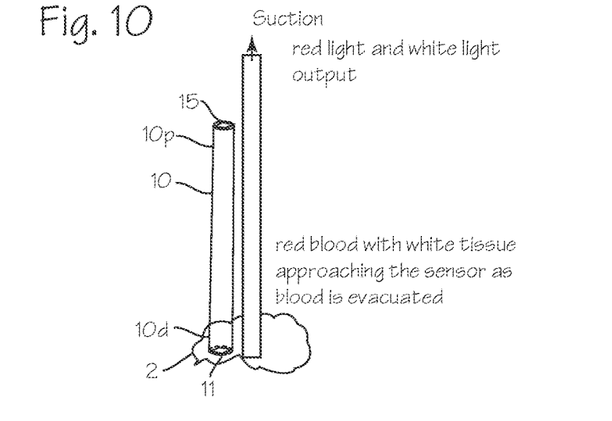

With the location of the blood mass confirmed, the surgeon can remove the blood mass. The surgeon may do this by aspiration, with suction applied through an aspiration catheter delivered to the blood mass. (This can be accomplished, depending on the configuration of the localization device, by delivering a suction catheter to the blood mass over the localizer (where the localizer comprises a wire), applying suction through the localizer (where the localizer also comprises an aspiration tube), swabbing the blood mass with swabs delivered through the localizer, or aspirating the blood mass with an aspiration tube deliver through the localizer (where the localizer comprises a cannula), etc.) Once a device for evacuating the blood mass is located within blood mass 2 the blood mass may be evacuated. The blood mass localizer may remain in place to monitor the progress of the blood mass evacuation. As a result of the removal of the blood mass, the surrounding brain tissue will collapse about the distal tip of the aspiration catheter and/or distal tip of the localizer, as illustrated in FIG. 10. As the blood mass is removed and the brain tissue collapses, the blood/brain margin will approach the color sensor assembly (that is, the amount of blood between the color sensor and the brain tissue will decrease) and the color sensor assembly will begin to detect increasing amount of white light. Consequently, the controller will operate the display to emit an increasing amount of white light, and a relatively decreasing amount of red light.

Although described above primarily in terms of an RGBW color sensor, the system can be implemented with a single-color sensor and/or a single-color LED, OLED or PLED (a single emitter or an array). For example, a red color sensor may be used alone, without the coincident use of green, blue and white sensors, to detect a red blood mass in surrounding white brain tissue. In this instance, the controller is preferably operable to operate the display to indicate that the probe tip is in brain tissue when the detected intensity of red light is low, below a predetermined threshold, and indicate that the probe tip is in blood when the detected intensity of red light is high, above a predetermined threshold, without also operating additional color sensors to positively detect brain tissue by detecting white light or other light.

The localizing device can be used to detect CSF at the probe tip, for locating the ventricles or cysts in the brain (or even the CSF between the dura and the brain. CSF is a clear, colorless fluid, such that with the color sensor assembly disposed within CSF, very little light emitted from the light source will be reflected by the CSF (compared to the light levels reflected by brain tissue). Thus, a low level of detected light, compared to the level detected in brain tissue, will provide an indication that the probe tip has entered a reservoir of CSF. That is, if all colors detectable by the color sensor assembly are detected at low intensity relative to brain tissue, this is indicative that the probe tip is in CSF. Thus, to detect colorless CSF, the controller is operable to receive color sensor data from the color sensor assembly, compare corresponding to the color of tissue surrounding the color sensor assembly, and operate the display to provide an indication to the user that the probe tip is disposed within CSF. Infrared light can also be used to determine that the distal end of the probe has entered cerebrospinal fluid, by providing an infrared light source and infrared color sensor. CSF is more transmissive to infrared light, compared to brain tissue, so that a lower level of infrared light detected by the infrared sensor during use indicates that the probe distal end has encountered CSF (normally this indicates that the probe tip has entered the sinus). Thus, when the information corresponding to the intensity of infrared detected by the infrared sensor assembly changes from information corresponding to the infrared reflectance/transmissivity of blood or brain tissue to information corresponding to the infrared reflectance/transmissivity of CSF, the controller operates the display to display a corresponding color (a false color, such as yellow or orange).

Instead of using light, the probe may be configured to use conductivity and conductivity sensors (or, conversely, the resistivity or impedance) to detect and differentiate tissues such as CSF, blood, and tumor from brain tissue. For example, CSF is significantly more conductive than brain tissue, so that the location of the probe tip within CSF can be determined on the basis of measured conductivity of tissue surrounding the probe tip. Brain tissue typically has conductivity of 0.25 S/m to 0.28 S/m (a resistivity of about 3.5 to 4 ohms/m). CSF has a conductivity of about 1.5 to 2 S/m (both at standard conditions of body temperature, tested at 40-70 Hz). To use a probe to localize a volume of CSF within the brain, an elongate probe, similar to that describe in FIG. 2, may be fitted with a pair of electrodes at the distal tip, and with the controller being operable to operate the electrodes receive electrical signals from the electrodes corresponding to the resistivity of the tissue surrounding the probe tip and the operate the display to provide output to the user to indicate whether the probe tip is disposed in brain tissue or CSF. The probe may also include a pressure sensor, operable to detect pressure exerted by body tissue on the sensor. The pressure sensor can be used to detect, or confirm, passage of the sensor, and probe tip, from the brain tissue into the sinus (the pressure of CSF in the cerebral sinus is typical lower than tissue pressure in the brain tissue).

The display described above is a convenient means for providing information to a user. It may be augmented with audible prompts or haptic feedback. For example, the system can include a speaker or annunciator (bell, buzzer, beeper or speaker), operable through the controller, to provide audible signals corresponding to the color detected by the color sensor. The annunciator can also function as a proximity warning, by providing a distinct audible signal (for example, beeping with increasing frequency) when the color sensor detects color indicative of an approaching margin during aspiration. (The controller can also be operable to operate the visual display to indicate the approaching margin, by flashing the display or providing other graphical output.)

The controller may comprise a digital or analog image signal processor (depending on the color sensor or image sensor) operable to convert the sensor data to input to the light or display, or it may comprise a microcontroller, a general-purpose computer, or the controller may comprise a special purpose computer, or similar device which comprises a processor and memory including program code with the memory, where the computer program code is configured with the processor to cause the system to perform the functions described throughout this specification. The controller may be disposed within the rod itself (as in FIGS. 2 and 11), in a handle at the proximal end of the probe (as in FIG. 12), or in an associated computer operably connected to the probe.

The probes can be provided with steering mechanism, operable to bend or steer the distal end of the probe, deflecting it from the longitudinal axis of the proximal portions of the probe. The steering mechanism can comprise a two-wire pullwire system with an appropriate actuating mechanism on the proximal end of the probe.

Figure 11:
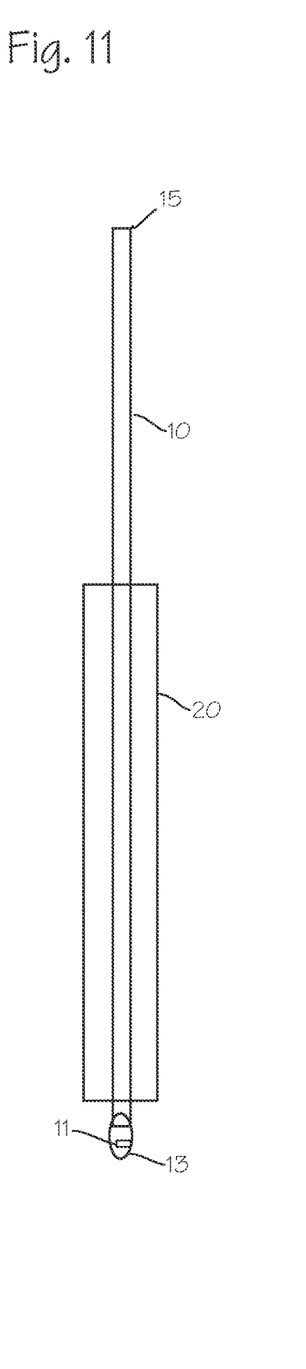
FIGS. 11, 12 and 13 illustrate different embodiments of the probe which can be used in different methods of accessing a blood mass.
Figure 12:
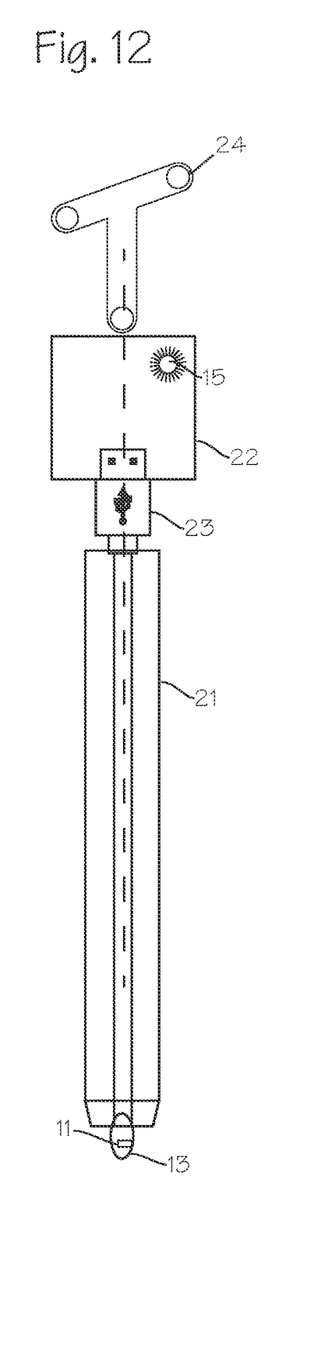
Figure 13:
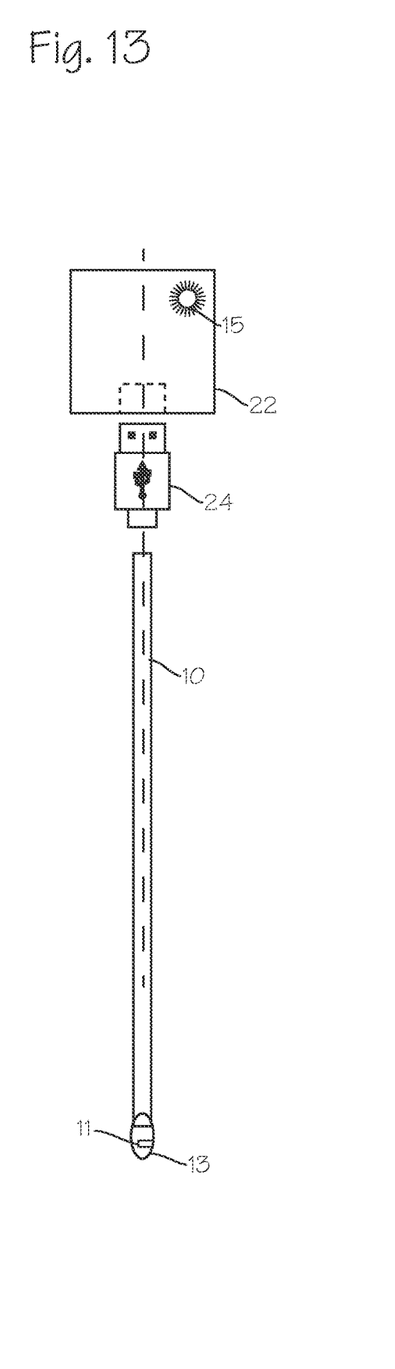

FIGS. 11, 12 and 13 illustrate different embodiments of the probe which can be used in different methods of accessing a blood mass. FIG. 11 illustrates the probe in a form that can be used in conjunction with a catheter or sheath, in an over-the-wire method, to access a blood mass in the brain. This probe may be a complete probe, though consisting of the rod, the color sensor assembly, the light source, which may be encapsulated in the lens 13, the display 15 disposed on the proximal end of the rod (on the proximal facing surface of the proximal end of the rod, with the display transverse dimension being smaller than the diameter of the rod, such that the display does not extend beyond the diameter of the rod) and the controller, all disposed on or within a probe of small diameter suitable for insertion through brain tissue and subsequent insertion of a sheath or cannula over the probe (while the probe remains in the brain). A surgeon may insert this probe into the brain, and, afterward, the surgeon may slip a short catheter 20 over the proximal end 10p of the rod, and push it distally over the entire probe until the catheter distal end is positioned in the brain proximate the blood mass. After the catheter distal end is placed proximate the blood mass, the surgeon removes the probe and may use any appropriate surgical tool (an aspirator, macerator, grasper, ablation probe) inserted through the catheter to remove the blood mass or otherwise treat the brain, or may apply suction to the catheter itself to aspirate the blood mass and remove it from the brain, inject medication or medically manage the source of bleeding and leave an indwelling drainage catheter and pressure monitor.

FIG. 12 illustrates a probe that can be used as an obturator in combination with a cannula or sheath. The probe is configured to fit into the lumen of a cannula or sheath 21 suitable for insertion into the brain while disposed over the probe. The distal end of the probe is sized to function as an obturator for use with the sheath. The lens 13 may serve as the atraumatic tip of the obturator. The probe comprises the rod 10, the color sensor assembly, and a proximal housing 22 which houses the control system, power source and the display 15 (which, in this embodiment may be a simple LED or equivalent lamp operable to display colors corresponding to the sensed color). The housing and its components may be permanently fixed to the rod, through any appropriate connector 23. This configuration may be assembled as an obturator/sheath combination, and a surgeon may insert the assembled system, with the tip of the probe extending slightly from the distal end of the sheath, until the distal end of the assembly is positioned as desired, based on the color sensed and the color displayed on the display indicates that the device is positioned as desired. The surgeon will then remove the probe from the sheath, and may use any appropriate surgical tool (an aspirator, macerator, grasper, ablation probe) inserted through the catheter to remove the blood mass or otherwise treat the brain, or may apply suction to the catheter itself to aspirate the blood mass and remove it from the brain, inject medication or medically manage the source of bleeding and leave an indwelling drainage catheter and pressure monitor.

FIG. 13 illustrates the probe in a form that can be used over-the-wire or as an obturator or as a stand-alone device. In the device of FIG. 13, the housing 22 and its components are releasably attached to rod 10 through a releasable electrical connector 24 which allows easy separation and reattachment of the components, intra-operatively, without the use of tools. The releasable electrical connector may, as shown in FIG. 13, be configured to allow detachment of the rod proximal and 10p from the connector, so that the rod may be used in the over the wire method described above, or may be configured to allow detachment of the rod and connector from the housing. The probe may also be configured with the rod permanently fixed to the housing, such that the components cannot be readily separated.

A neuro-navigation marker 25, shown in FIG. 12, may be incorporated into each embodiment illustrated.

The devices and methods described below provide for a method for localizing a blood mass in a patient's brain by providing an elongate probe having a distal end and a proximal end, with a color sensor assembly operable to detect a plurality of colors in tissue proximate the distal end of the probe and generate a signal corresponding each of the plurality of colors detected by the color sensor assembly and then providing a display operable to display information corresponding to the color detected by the color sensor assembly, and then inserting the distal end of the probe into the patient's brain, and then advancing the distal end of the probe through the patient's brain, while operating the display to display information corresponding to the intensity of each color detected by the color sensor assembly observing the display, and then determining that the distal end of the probe is disposed within brain tissue or a blood mass, based on the displayed information corresponding to the intensity of each color detected by the color sensor assembly.

The devices and methods described below provide for a device for localizing a blood mass in a patient's brain. The localizing device includes an elongate probe having a distal end and a proximal end and one or more color sensors and a light emitter on the distal end of the probe. The color sensors produce a signal corresponding to the characteristics of light reflected into the color sensors. A controller is operatively connected to the color sensors to convert the signal to data suitable for display to a user, and a display is operatively connected to the controller for visualizing data corresponding to the tissue reflecting light to the color sensors.

In the context of this application, localize or localization means to find or identify the location and extent of a mass such as an intracerebral blood mass in brain tissue, and the term localizer refers to a device operable to be inserted into the body to determine the location of a type of tissue within a mass of other tissue.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method for localizing a blood mass in a patient's brain comprising the steps:
   providing an elongate probe having a distal end and a proximal end, with a color sensor assembly operable to detect color in tissue proximate the distal end of the probe;
   providing a display operable to display information corresponding to color detected by the color sensor assembly;

inserting the distal end of the probe into the patient's brain;

advancing the distal end of the probe through the patient's brain, while operating the display to display information corresponding to color detected by the color sensor assembly while observing the display; and determining that the distal end of the probe is disposed within brain tissue or a blood mass, based on the displayed information corresponding to the intensity of color detected by the color sensor assembly, and, after determining that the distal end of the probe is disposed within a blood mass;

inserting a catheter into the brain over the proximal end of the probe, pushing the catheter distally over the probe until a distal end of the catheter is positioned in the brain proximate the blood mass.

2. The method of claim 1, further comprising the step of removing the probe from the catheter, leaving a lumen of the catheter open for subsequent access to the blood mass through the catheter.

3. The method of claim 1, further comprising the step of inserting a surgical tool through the catheter and into the brain.

4. The method of claim 1, further comprising the step of applying suction through the catheter to aspirate the blood mass and remove it from the brain.

5. The method of claim 1, further comprising the step of injecting medication through the catheter and into the brain.

6. The method of claim 1, further comprising the step of inserting a pressure monitor through the catheter and into the brain.

7. A method for localizing a blood mass in a patient's brain comprising the steps:

providing an elongate probe having a distal end and a proximal end, with a color sensor assembly operable to detect color in tissue proximate the distal end of the probe, and a display operable to display information corresponding to color detected by the color sensor assembly, said display having a transverse dimension smaller than a diameter of the probe;

inserting the distal end of the probe into the patient's brain;

advancing the distal end of the probe through the patient's brain, while operating the display to display information corresponding to color detected by the color sensor assembly while observing the display; and determining that the distal end of the probe is disposed within brain tissue or a blood mass, based on the displayed information corresponding to the intensity of color detected by the color sensor assembly, and, after determining that the distal end of the probe is disposed within a blood mass;

inserting a catheter into the brain over the proximal end of the probe, pushing the catheter distally over the probe until a distal end of the catheter is positioned in the brain proximate the blood mass.

8. The method of claim 7, further comprising the step of removing the probe from the catheter, leaving a lumen of the catheter open for subsequent access to the blood mass through the catheter.

9. The method of claim 7, further comprising the step of inserting a surgical tool through the catheter and into the brain.

10. The method of claim 7, further comprising the step of applying suction through the catheter to aspirate the blood mass and remove the blood mass from the brain.

11. The method of claim 7, further comprising the step of injecting medication through the catheter and into the brain.

12. The method of claim 7, further comprising the step of inserting a pressure monitor through the catheter and into the brain.

13. A method for localizing a blood mass in a patient's brain comprising the steps:

providing an elongate probe having a distal end and a proximal end, with a color sensor assembly operable to detect color in tissue proximate the distal end of the probe;

providing a display operable to display information corresponding to color detected by the color sensor assembly, wherein said display is releasably attached to the proximal end of the probe;

inserting the distal end of the probe into the patient's brain;

advancing the distal end of the probe through the patient's brain, while operating the display to display information corresponding to color detected by the color sensor assembly while observing the display; and determining that the distal end of the probe is disposed within brain tissue or a blood mass, based on the displayed information corresponding to the intensity of color detected by the color sensor assembly, and, after determining that the distal end of the probe is disposed within a blood mass;

detaching the display from the proximal end of the probe; and thereafter inserting a catheter into the brain over the proximal end of the probe, pushing the catheter distally over the entire probe until a distal end of the catheter is positioned in the brain proximate the blood mass.

14. The method of claim 13, further comprising the step of removing the probe from the catheter, leaving a lumen of the catheter open for subsequent access to the blood mass through the catheter.

15. The method of claim 13, further comprising the step of inserting a surgical tool through the catheter and into the brain.

16. The method of claim 13, further comprising the step of applying suction through the catheter to aspirate the blood mass and remove it from the brain.

17. The method of claim 13, further comprising the step of injecting medication through the catheter and into the brain.

18. The method of claim 13, further comprising the step of inserting a pressure monitor through the catheter and into the brain.

* * * * *